US010817841B1

(12) United States Patent
Weiss et al.

(10) Patent No.: US 10,817,841 B1
(45) Date of Patent: *Oct. 27, 2020

(54) SYSTEM AND METHOD FOR A NEW PRESCRIPTION SCAN

(71) Applicant: WALGREEN CO., Deerfield, IL (US)

(72) Inventors: Benjamin Weiss, Chicago, IL (US); Jon Turkington, Huntley, IL (US); Adam Crouch, Chicago, IL (US); Richard S. Majka, Park Ridge, IL (US); Atul Singh, Vernon Hills, IL (US)

(73) Assignee: WALGREEN CO., Deerfield, IL (US)

( * ) Notice: Subject to any disclaimer, the term of this patent is extended or adjusted under 35 U.S.C. 154(b) by 157 days.

This patent is subject to a terminal disclaimer.

(21) Appl. No.: 16/052,258

(22) Filed: Aug. 1, 2018

Related U.S. Application Data

(63) Continuation of application No. 14/190,323, filed on Feb. 26, 2014, now Pat. No. 10,074,076.

(51) Int. Cl.
*G16H 20/10* (2018.01)
*G06Q 10/10* (2012.01)
(Continued)

(52) U.S. Cl.
CPC ............ *G06Q 10/10* (2013.01); *G06F 19/00* (2013.01); *G06Q 20/4016* (2013.01); *G16H 20/10* (2018.01)

(58) Field of Classification Search
CPC .... G06Q 10/10; G06Q 20/4016; G06F 19/00; G16H 20/10
See application file for complete search history.

(56) References Cited

U.S. PATENT DOCUMENTS 8,280,833 B2 * 10/2012 Miltonberger ....... G06Q 10/067
706/45
8,392,210 B2 * 3/2013 Beraja ................. H04W 4/029
705/2
(Continued)

FOREIGN PATENT DOCUMENTS

WO WO-2001086574 A2 11/2001

OTHER PUBLICATIONS

McCauley et al., U.S. Appl. No. 13/910,697, entitled "System and Method for Express Refill via Short Range Communication," filed Jun. 5, 2013.
(Continued)

*Primary Examiner* — Eliza A Lam
(74) *Attorney, Agent, or Firm* — Marshall, Gerstein & Borun LLP; Randall G. Rueth

(57) ABSTRACT

A method and system may provide a new prescription order interface which allows a customer to order one or more new prescription medications in a quick and easy manner from a remote location using a computer or mobile device. The customer provides a new paper prescription image that includes the prescription data for a pharmacy to fill the new prescription order. The new paper prescription image is received by a server and a default pickup store and a default pickup time are determined. The server also determines whether there is a high risk that the new prescription order is fraudulent by comparing a signature in the new paper prescription image to stored signatures associated with the prescriber, and comparing distances between the locations of the customer's web-enabled device, the pharmacy, and the prescriber. The system may be accessed through a series of web pages and/or via an application.

20 Claims, 13 Drawing Sheets

(51) Int. Cl.
*G06Q 20/40* (2012.01)
*G06F 19/00* (2018.01)

(56) References Cited

U.S. PATENT DOCUMENTS

| | | | |
|---|---|---|---|
| 8,626,530 | B1 | 1/2014 | Tran et al. |
| 9,779,403 | B2 * | 10/2017 | Ranganath ............ G06Q 20/405 |
| 2005/0182656 | A1 | 8/2005 | Morey |
| 2008/0015897 | A1 | 1/2008 | Moradi et al. |
| 2009/0006126 | A1 | 1/2009 | Champigny |
| 2013/0275303 | A1 | 10/2013 | Fiore et al. |
| 2014/0063311 | A1 | 3/2014 | McCauley et al. |
| 2014/0129420 | A1 | 5/2014 | Howe |
| 2014/0137199 | A1 | 5/2014 | Hefetz |
| 2014/0172439 | A1 | 6/2014 | Conway et al. |

OTHER PUBLICATIONS

McCauley et al., U.S. Appl. No. 13/555,350, entitled "System and Method for Prescription Medication Transfer Order," filed Jul. 23, 2012.
McCauley, U.S. Appl. No. 13/478,833, entitled "System and Method for Automatically Generating Prescription Reminders from a Scanned Barcode," filed Jun. 23, 2012.
Taneja, U.S. Appl. No. 13/738,556, entitled "System and Method for Automatically Generating a Prescription Refill Order via a Reply Electronic Message," filed Jan. 10, 2013.
Tran et al., U.S. Appl. No. 12/869,983 entitled "Method and Apparatus for Express Refill," filed Aug. 27, 2010.
Office Action for U.S. Appl. No. 14/190,323, dated Aug. 26, 2016.
Office Action for U.S. Appl. No. 14/190,323, dated Oct. 5, 2017.
Office Action for U.S. Appl. No. 14/190,323, dated Feb. 28, 2018.
Office Action for U.S. Appl. No. 14/190,323, dated Feb. 17, 2017.
Search Report and Written Opinion for International application No. PCT/US2015/017187, dated May 29, 2015.

* cited by examiner

PRESCRIBER SIGNATURE ON NEW
PAPER PRESCRIPTION IMAGE

DIGITAL FINGERPRINT IN
PRESCRIBER DATABASE

SYSTEM AND METHOD FOR A NEW PRESCRIPTION SCAN

CROSS-REFERENCE TO RELATED APPLICATIONS

This application is a continuation of and claims priority to U.S. application Ser. No. 14/190,323, filed on Feb. 26, 2014, entitled "System and Method for a New Prescription Scan," the entire contents of which are hereby expressly incorporated by reference.

TECHNICAL FIELD

The present disclosure generally relates to a system and method for filling new prescription medications and, more particularly to a new prescription method and system allowing a customer to order one or more new paper prescriptions online, in an efficient and expeditious manner.

BACKGROUND

In the past, a patient (or customer) wishing to order a new prescription medication visited a pharmacy to drop off the paper prescription in person. In some instances, a patient could request a new prescription medication by mail, by phone or by facsimile, which would require the pharmacy staff to call the prescriber to confirm or initiate a legal prescription.

In any event, the systems currently in place require a patient who wishes to order a new paper prescription to call, visit, mail or send a facsimile to the pharmacy, all of which can be very time consuming processes. In many instances, a customer must drop the new paper prescription off at the pharmacy and wait 20-30 minutes before the corresponding prescription medication is ready. In addition, many pharmacists are required to examine a new paper prescription to determine whether the new paper prescription is fraudulent because, for example, the prescribing physician's signature was forged, the prescriber is not a licensed physician, etc. Besides for the additional amount of time this takes, pharmacists also may make errors in judgment and fill some fraudulent prescriptions while refusing to fill other legitimate prescriptions.

SUMMARY

In an embodiment, a method of detecting fraud when filling a new prescription order for one or more prescription medications is provided. The method includes storing, for each of a plurality of prescribers, one or more signatures associated with a prescriber, receiving from a web-enabled device of a customer, over a network, an image of a new paper prescription for the customer, determining a pharmacy at which to fill a new prescription order corresponding to the new paper prescription, and determining prescription data based on the image of the new paper prescription, where the prescription data includes an identification of a prescriber who wrote or printed the new paper prescription. The method further includes comparing a signature in the image of the new paper prescription to the one or more stored signatures associated with the prescriber, determining a first risk of prescription fraud based on the compared signatures, determining a location of the web-enabled device, a location of the pharmacy, and a location of the prescriber, and determining a second risk of prescription fraud by assigning weights to a plurality of distances between the location of the web-enabled device, the location of the pharmacy, and the location of the prescriber and combining the plurality of distances and the assigned weights to generate a score indicative of the second risk of prescription fraud. Furthermore, the method includes combining the first and seconds risks of prescription fraud to generate an overall risk of prescription fraud, and when the overall risk of prescription fraud does not exceed a threshold amount of risk, transmitting, via the network, information to be displayed in an order review page on the web-enabled device, and receiving, from the web-enabled device and via the network, a confirmation to submit the new prescription order.

In another embodiment, a system for detecting fraud when filling a new prescription order for one or more prescription medications is provided. The system includes a communication network, and one or more server computers communicatively coupled to the communication network. At least one of the server computers is configured to store for each of a plurality of prescribers, one or more signatures associated with a prescriber, receive from a web-enabled device communicatively coupled to the communication network, an image of a new paper prescription for a customer, determine a pharmacy at which to fill a new prescription order corresponding to the new paper prescription, and determine prescription data based on the image of the new paper prescription, where the prescription data includes an identification of a prescriber who wrote or printed the new paper prescription. At least one of the server computers is further configured to compare a signature in the image of the new paper prescription to the one or more stored signatures associated with the prescriber, determine a first risk of prescription fraud based on the compared signatures, determine a location of the web-enabled device, a location of the pharmacy, and a location of the prescriber, and determine a second risk of prescription fraud by assigning weights to a plurality of distances between the location of the web-enabled device, the location of the pharmacy, and the location of the prescriber and combining the plurality of distances and the assigned weights to generate a score indicative of the second risk of prescription fraud. Additionally, at least one of the server computers is configured to combine the first and seconds risks of prescription fraud to generate an overall risk of fraud, and when the overall risk of prescription fraud does not exceed a threshold amount of risk, transmit to the web-enabled device from the server computer, via the network, information to be displayed in an order review page on the web-enabled device, and receive from the web-enabled device, via the network, a confirmation to submit the new prescription order.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Generally speaking, a new prescription order system allows a customer to scan a new paper prescription, handwritten or printed by a healthcare provider (also referred to herein as a "prescriber"), via a web-enabled device, and the system automatically retrieves prescription data associated with the new paper prescription. To scan a new paper prescription, the customer launches a client application on the web-enabled device, logs in to the system and subsequently navigates to an image capture screen within the client application. The client application then scans the new paper prescription using the image capture screen. As a result, the new prescription order system automatically retrieves prescription data, and allows the customer to select a pharmacy location along with a pickup date and time for retrieving the new prescription order. In addition to transmitting the order to the selected pharmacy, the system performs fraud analysis to ensure the new prescription order is not fraudulent.

To perform the fraud analysis, the system calculates the distances between the web-enabled device, the selected pharmacy and the office of the prescriber who wrote or printed the new paper prescription. The system also compares the signature on the new paper prescription to previously stored signatures for the prescriber. If the combined distances between the web-enabled device, the selected pharmacy and the office of the prescriber exceed a predetermined threshold or the signatures do not generate a match, the system determines a high risk of fraud and may not allow the customer to transmit the order to the selected pharmacy.

Figure 1A:
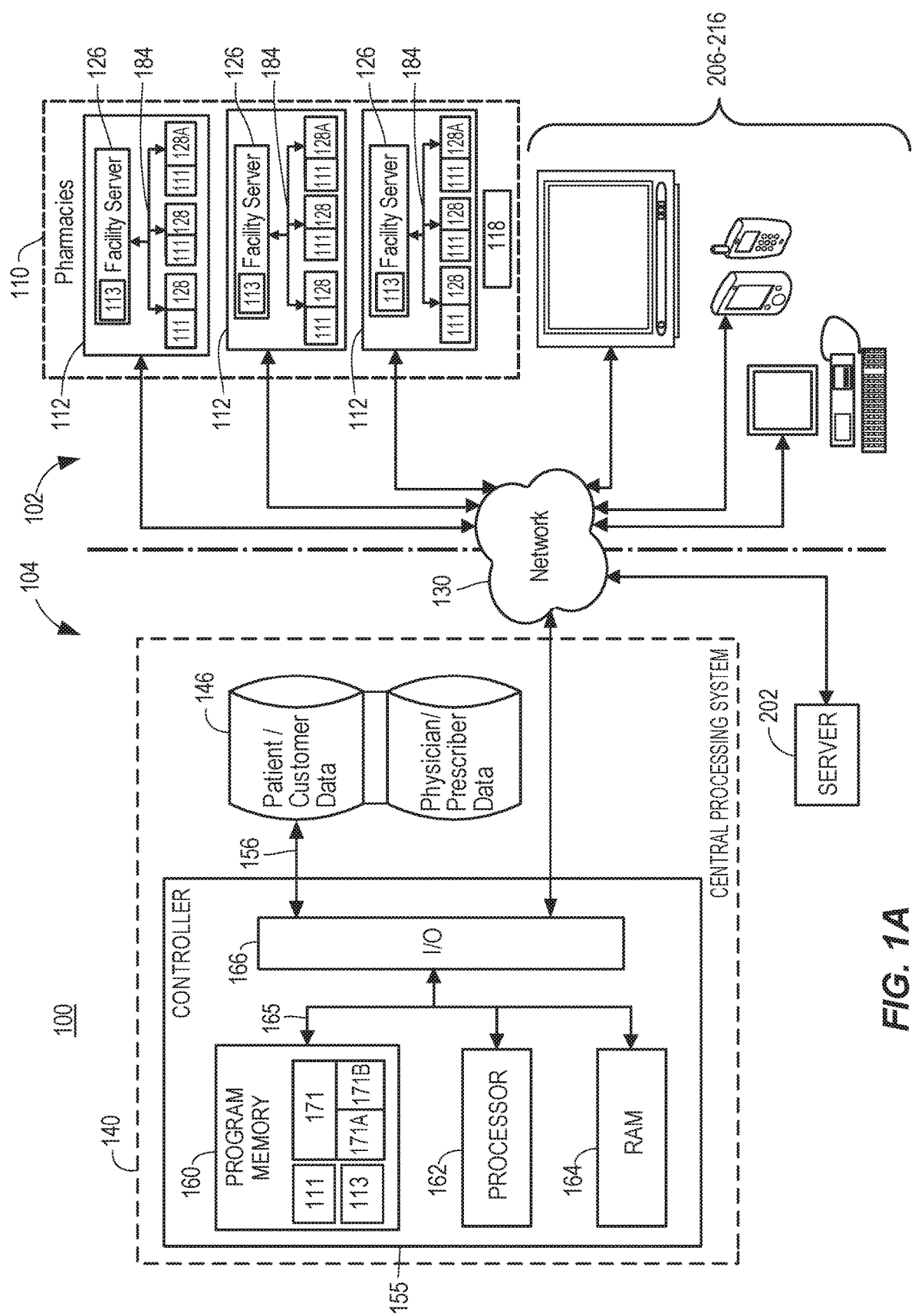
FIG. 1A illustrates a block diagram of a computer network and system on which an exemplary new prescription order system and method may operate in accordance with the described embodiments.

FIG. 1A illustrates various aspects of an exemplary architecture implementing a new prescription order system 100. In particular, FIG. 1A illustrates a block diagram of the new prescription order system 100. The high-level architecture includes both hardware and software applications, as well as various data communications channels for communicating data between the various hardware and software components. The new prescription order system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new paper prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers. Web-enabled devices 206-216 (e.g., personal computers, cellular phones, smart phones, web-enabled televisions, etc.) may be communicatively connected to the pharmacies 112 and to a system 140 through a digital network 130, as described below.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the web-enabled devices 206-216 may be excluded from direct access to the back-end components 104. In some embodiments, the pharmacies 112 may communicate with the back-end components via the digital network 130. In other embodiments, the pharmacies 112 and web-enabled devices 206-216 may communicate with the back-end components 104 via the same digital network 130, but digital access rights, IP masking, and other network configurations may deny access to the web-enabled devices 206-216.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. In addition to one or more servers 202 (described below), the back-end components 104 include the central processing system 140 within a central processing facility, such as, for example, the central processing facility described in U.S. Pat. No. 8,175,891 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the new prescription order system 100, in addition to other software applications. The central processing system 140 further includes a database 146. The database 146 is adapted to store data related to the operation of the new prescription order system 100 (e.g., patient profile data including diagnoses, past healthcare product and medication purchases and prescription histories as well as physician profile data including DEA number, previously written prescriptions, past signatures, office location, etc.). The central processing system 140 may access data stored in the database 146 when executing various functions and tasks associated with the operation of the new prescription order system 100.

Although FIG. 1A depicts the new prescription order system 100 as including the central processing system 140 in communication with three pharmacies 112, and various web-enabled devices 206-216 it should be understood that different numbers of processing systems, pharmacies, and devices may be utilized. For example, the digital network 130 (or other digital networks, not shown) may interconnect the central processing system 140 to a plurality of included central processing systems 140, hundreds of pharmacies 112, and thousands of web-enabled devices 206-216. According to the disclosed example, this configuration may provide several advantages, such as, for example, enabling near real-time uploads and downloads of information as well as periodic uploads and downloads of information. This provides for a primary backup of all the information generated in the new prescription process. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1A as including two modules, 171A and 171B, the software 171 may include any number of modules accomplishing tasks related to pharmacy operation including, for example, receiving prescription orders, managing prescription workflow, etc. The central processing system 140 implements a server application 113 for providing data to a user interface application 111 operating on the workstations 128.

Figure 1B:
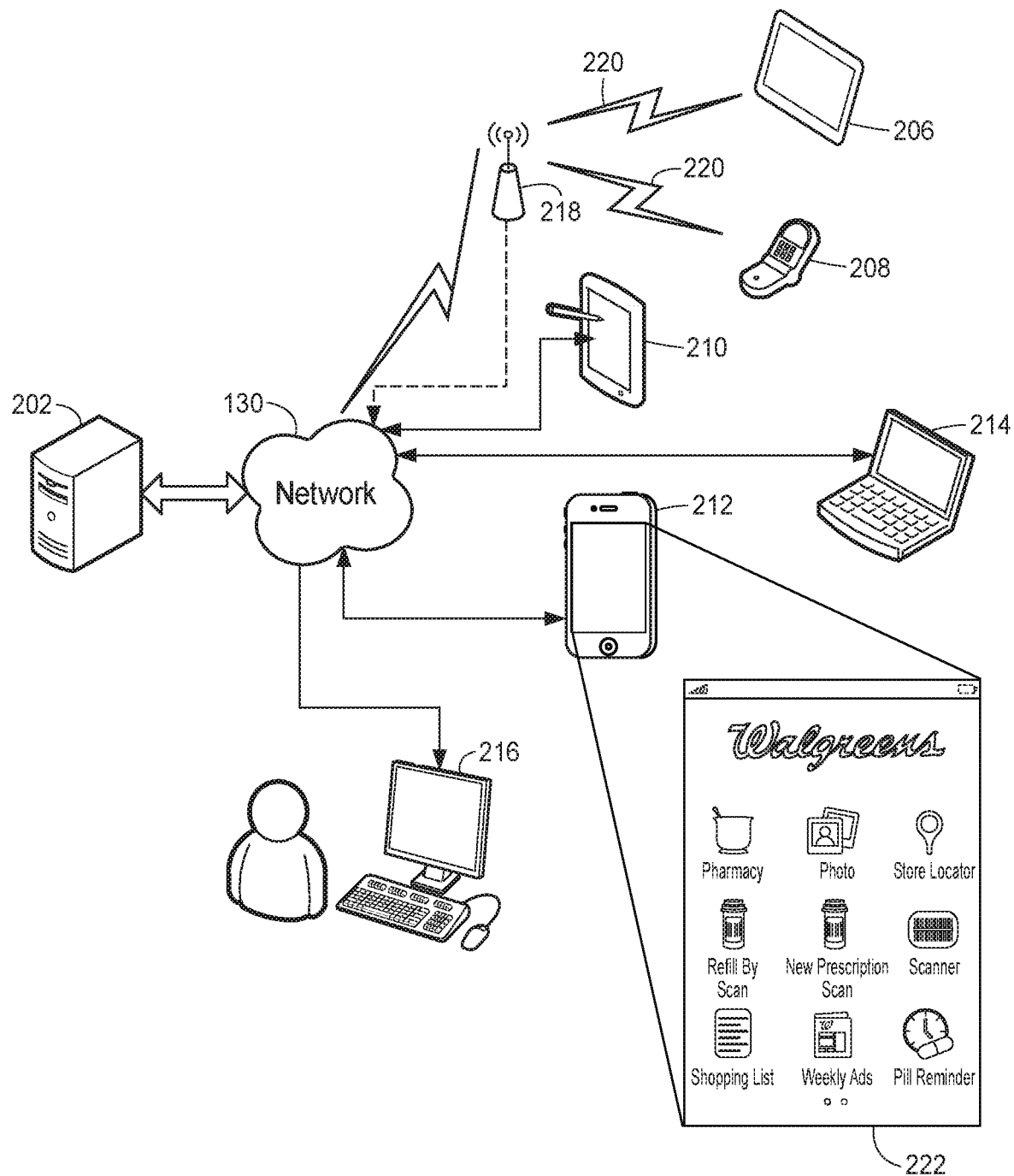
FIG. 1B illustrates web-enabled devices and associated equipment that may operate with a network and a server.

For purposes of implementing the new prescription order system 100, the user interacts with the server 202 and the pharmacy systems (e.g., the central processing system 140) via a web-enabled device 206-216 (e.g., mobile device application, etc.), a specialized application, or a plurality of web pages. FIG. 1B depicts the server 202 connected via the network 130 to the web-enabled devices 206-216 through which a user may initiate and interact with the new prescription order system 100 (as shown in FIG. 1A). The web-enabled devices 206-216 may include, by way of example, a tablet computer 206, a web-enabled cell phone 208, a personal digital assistant (PDA) 210, a mobile device smart-phone 212 also referred to herein as a "mobile device," a laptop computer 214, a desktop computer 216, a portable media player (not shown), a wearable computing device such as Google Glass™ (not shown), etc. Of course, any web-enabled device appropriately configured may interact with the new prescription order system 100. The web-enabled devices 206-216 need not necessarily communicate with the network 130 via a wired connection. In some instances, the web-enabled devices 206-216 may communicate with the network 130 via wireless signals 220 and, in some instances, may communicate with the network 130 via an intervening wireless or wired device 218, which may be a wireless router, a wireless repeater, a base transceiver station of a mobile telephony provider, etc. Each of the web-enabled devices 206-216 may interact with the server 202 to receive web pages, application views or server data from the server 202 and may display the web pages, application views or server data via a client application (described below). For example, the mobile device 212 may display a home screen 222 (i.e., the root or start page at which users enter the client application) of the client application to user, may receive an input from the user, and may interact with the server 202 depending on the type of user-specified input. It will be appreciated that although only one server 202 is depicted in FIG. 1B, multiple servers 202 may be provided for the purpose of distributing server load, serving different web pages, implementing different portions of the pharmacy web interface, etc. These multiple servers 202 may include a web server, an entity-specific server (e.g. an Apple® server, etc.), a server that is disposed in a retail or proprietary network, an independent third-party server that is not under the control of the entity, etc.

Figure 1C:
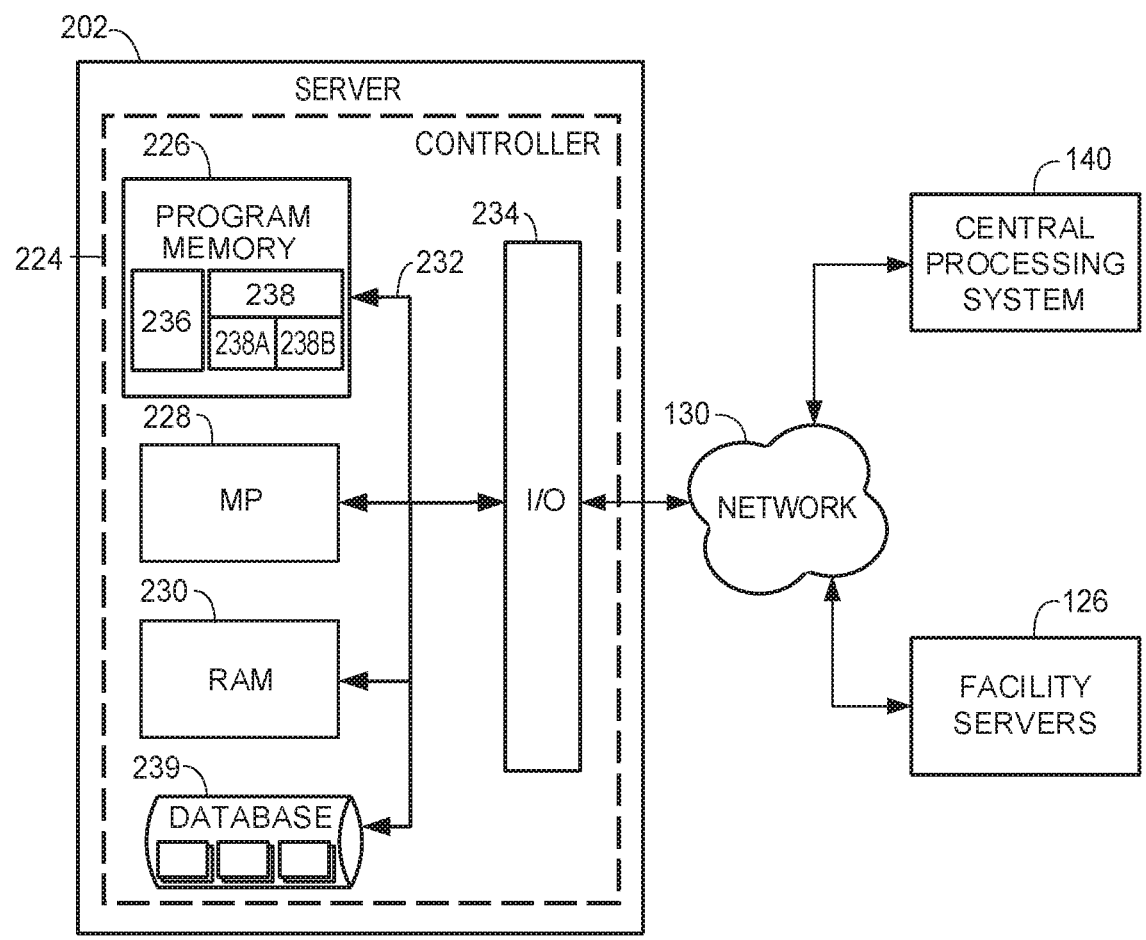
FIG. 1C illustrates a block diagram of an exemplary server.

Turning now to FIG. 1C, the server 202, like the facility server 126, includes a controller 224. Similar to the controllers 155 and 170, the controller 224 includes a program memory 226, a microcontroller or a microprocessor (MP) 228, a random-access memory (RAM) 230, and an input/output (I/O) circuit 234, all of which are interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as customer web profiles, prescriber web profiles, product data, mobile device application data, web page templates and/or web pages, and other data necessary to interact with the user through the network 130. As discussed with reference to the controllers 155 and 170, it should be appreciated that although FIG. 1C depicts only one microprocessor 228, the controller 224 may include multiple microprocessors 228. Similarly, the memory of the controller 224 may include multiple RAMs 230 and multiple program memories 226. Although the FIG. 1C depicts the I/O circuit 234 as a single block, the I/O circuit 234 may include a number of different types of I/O circuits. The controller 224 may implement the RAM(s) 230 and the program memories 226 as semiconductor memories, magnetically readable memories, and/or optically readable memories, for example.

In addition to being connected through the network 130 to the web-enabled devices 206-216, as depicted in FIG. 1B, FIG. 1C illustrates that the server 202 may also be connected through the network 130 to the central processing system 140 and/or one or more facility servers 126. As described below, the connection of the server 202 to the central processing system 140 assists in facilitating some of the functionality of the new prescription order process. As a result, the server 202 may act as a routing or interfacing server between the plurality of web-enabled devices 206-216 and a destination server, namely, the central processing system 140. For example, the server 202 may be configured to communicate the central processing system 140 and with the web-enabled device 206-216 via a multitude of protocols, such as packet-switched protocols, web services, web APIs, etc. The server 202 may also convert (if necessary) and route client application data (not shown) to the appropriate server, such as the central process system 140 for example. Additionally, the server 202 may act as the destination server and need not route any data from the web-enabled device 206-216.

As shown in FIG. 1C, the program memory 226 and/or the RAM 230 may store various applications for execution by the microprocessor 228. For example, a user-interface application 236 may provide a user interface to the server 202, which user interface may, for example, allow a network administrator to configure, troubleshoot, or test various aspects of the server's operation, or otherwise to access information thereon. A server application 238 operates to populate and transmit client application data and web pages to the web-enabled devices 206-216, receive information from the user transmitted back to the server 202, and forward appropriate data to the central processing system 140 and the facility servers 126, as described below. Like the software 171 of FIGS. 1A and 1B, the server application 238 may be a single module 238 or a plurality of modules 238A, 238B. While the server application 238 is depicted in FIG. 1C as including two modules, 238A and 238B, the server application 238 may include any number of modules accomplishing tasks related to implantation of the server 202. By way of example, the module 238A may populate and transmit the client application data and/or may receive and evaluate inputs from the user to receive a data access request, while the module 238B may communicate with one or more of the back end components 104 to fulfill a data access request.

Figure 1D:
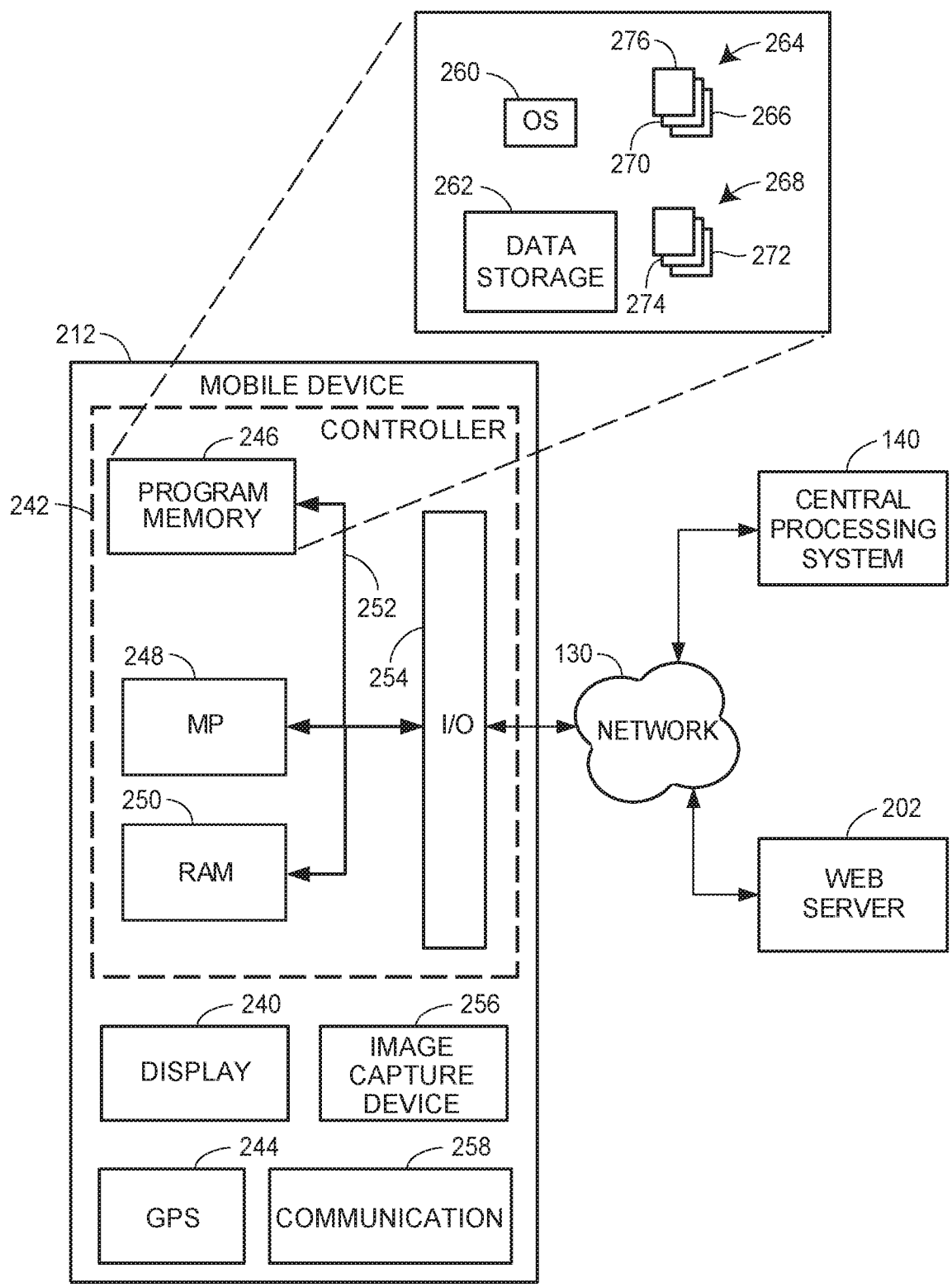
FIG. 1D illustrates a block diagram of an exemplary mobile device.

Referring now to FIG. 1D, the mobile device 212 (or any of the web-enabled devices 206-216) includes a display 240, a Global Positioning System (GPS) unit 244, a communication unit 258, an image capture device 256, a user-input device (not shown), and, like the server 202, a controller 242. Similar to the controllers 155 and 224, the controller 242 includes a program memory 246, one or more microcontroller or a microprocessor (MP) 248, a random-access memory (RAM) 250, and an input/output (I/O) circuit 254, all of which are interconnected via an address/data bus 252. The program memory 246 includes an operating system 260, a data storage 262, a plurality of software applications 264, and a plurality of software routines 268. The operating system 260, for example, may include one of a plurality of mobile platforms such as the iOS®, Android™, Palm® webOS, Windows Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 262 may include data such as user profiles, application data for the plurality of applications 264, routine data for the plurality of routines 268, and other data necessary to interact with the server 202, the facility servers 126, or the server applications 113 through the digital network 130. In some embodiments, the controller 242 may also include, or otherwise be communicatively connected to, other data storage mechanisms (e.g., one or more hard disk drives, optical storage drives, solid state storage devices, etc.) that reside within the mobile device 212.

The GPS unit 244 may use "Assisted GPS" (A-GPS), satellite GPS, or any other suitable global positioning protocol or system that locates the position the mobile device 212. For example, A-GPS utilizes terrestrial cell phone towers or wi-fi hotspots (e.g., wireless router points) to more accurately and more quickly determine location of the mobile device 212 while satellite GPS generally are more useful in more remote regions that lack cell towers or wifi hotspots. The communication unit 258 may communicate with the server 202 via any suitable wireless communication protocol network, such as a wireless telephony network (e.g., GSM, CDMA, LTE, etc.), a wi-fi network (802.11 standards), a WiMAX network, a Bluetooth network, etc. The image capture device 256 may be a built-in camera within the mobile device 212 or may be an external camera, such as a webcam, that is communicatively coupled with the mobile device 212 (or any other web-enabled device 206-216). The user-input device (not shown) may include a "soft" keyboard that is displayed on the display 240 of the mobile device 212, an external hardware keyboard communicating via a wired or a wireless connection (e.g., a Bluetooth keyboard), an external mouse, or any other suitable user-input device. As discussed with reference to the controllers 155 and 224, it should be appreciated that although FIG. 1D depicts only one microprocessor 248, the controller 242 may include multiple microprocessors 248. Similarly, the memory of the controller 242 may include multiple RAMs 250 and multiple program memories 246. Although the FIG. 1D depicts the I/O circuit 254 as a single block, the I/O circuit 254 may include a number of different types of I/O circuits. The controller 242 may implement the RAM(s) 250 and the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 242, in addition to other software applications. One of the plurality of applications 264 may be a client application 266 that may be implemented as a series of machine-readable instructions for performing the various tasks associated with receiving information at, displaying information on, and transmitting information from the mobile device 212. One of the plurality of applications 264 may be a native application or web browser 270, such as Apple's Safari®, Google Android™ mobile web browser, Microsoft Internet Explorer® for Mobile, Opera Mobile™, that may be implemented as a series of machine-readable instructions for receiving, interpreting, and displaying web page information or application data from the server 202, the facility servers 126, or the server applications 113 while also receiving inputs from the user. Another application of the plurality of applications may include an embedded web browser 276 that may be implemented as a series of machine-readable instructions for receiving, interpreting, and displaying web page information from the servers 202, 126, or server applications 113 within the client application 266. One of the plurality of routines may include an image capture routine 272 that coordinates with the image capture device 256 to retrieve image data for use with one or more of the plurality of applications, such as the client application 266, or for use with other routines. Another routine in the plurality of routines may include a new paper prescription scanning routine 274 that determines a new prescription order from the image data and translates the new prescription order into prescription data. Likewise, the new paper prescription scanning routine 274 coordinates with the image capture routine to obtain image data and process the image data into prescription data for use with the client application 266.

Preferably, a customer, a patient, or a user may launch the client application 266 from a web-enabled device, such as one of the web-enabled devices 206-216, to access the server 202 cooperating with the central processing system 140 and the pharmacies 110 to implement the new prescription order system 100. Additionally, the customer, the patient, or the user may also launch or instantiate any other suitable user interface application (e.g., the native application or web browser 270, or any other one of the plurality of software applications 264) to access the server 202, the facility servers 126, or the server applications 113 to realize the new prescription order system 100. As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "customer" is used primarily so as to avoid confusion. Generally, the term "user" is used when referring to a person who is operating one of the web-enabled devices 206-216 and is not exclusive of the terms "customer" and "patient."

As described above, the database 146, illustrated in FIG. 1A, includes various information about the pharmacy's customers, prescribing physicians, the prescriptions filled by the pharmacy and prescription medications. Customer records are among the exemplary data that the new prescription order system 100 may store on the database 146. A customer record contains important information about the customer and the various pharmacy services that have been invoked by, or on behalf of, the customer in a customer profile. The customer profile includes basic biographical information about the customer, such as a customer name, a customer address, a customer phone number, a customer birth date, customer prescription history, a list of authorized patients the customer can fill prescriptions on behalf of, a default pickup store for the customer, a default pickup time and date, customer insurance information etc. Prescribing physician records may also be stored on the database 146. Prescribing physician records may include a physician name, a practice name, a physician DEA number, a physician phone number, a physician office address, previously written prescriptions by the physician, one or more physician signatures, etc.

As shown in FIG. 1B, to access the server 202, the facility servers 126, or the server applications 113, the user executes the client application 266 on one of the web-enabled devices 206-216, such as the mobile device 212. Using the client application 266, the user may request server data (not shown) by navigating a series of client application screens, such as the home screen 222 of the client application 266. FIGS. 2, 3 and 4A-H depict client application pages or screens that the server 202, the facility servers 126, or the server applications 113 may transmit in various embodiments of the new prescription order system 100. In any event, the user may launch the client application 266 from one of the web-enabled devices 206-216 via any suitable manner, such as touch-selecting a client application icon (not shown) on the display 240 of the mobile device 212, double-clicking on the client application icon via a mouse of a computer 216 or a trackpad (not shown) of a laptop 214. After the user launches the client application 266, the home screen 222 of the client application 266 is displayed to the user on the mobile device 212.

Figure 2:
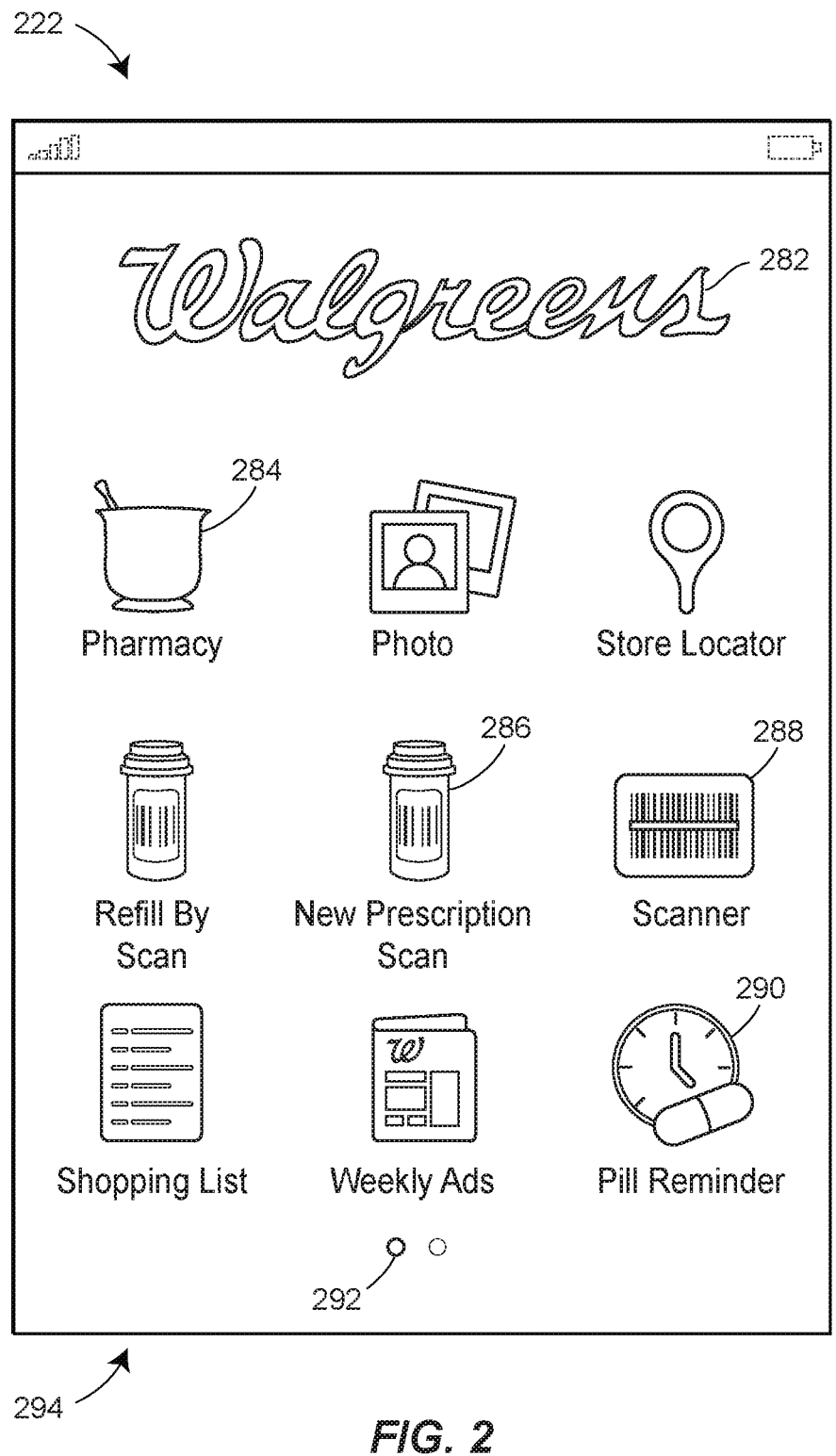
FIG. 2 depicts a home screen of a client application.

With reference now to FIG. 2, a first menu page 294 of the home screen 222 of the client application 266, for example, is displayed to the user on the mobile device 212. The home screen 222 may include a company logo 282, a pharmacy services link 284, a new prescription scan link 286, a scanner link 288, a pill reminder link 290, and a menu page indicator 292. In FIG. 2, the menu page indicator 292 denotes that only the first menu page of the home screen 222 is currently being displayed. The user may touch-swipe on the display 240 of the mobile device 212 to view the second menu page (not shown) of the home screen 222. The second menu page of the home screen 222 may display additional links that cannot be accommodated on the first menu page of the home screen 222 (e.g., a shopping link, etc.). In another embodiment, using the client application 266, the user may request and navigate a series of web pages or application views transmitted, preferably in a secure manner (e.g., using Hypertext Transfer Protocol Secure, known as "HTTPS"), by the server 202 to the web-enabled device 206-216. These web pages or application views may be interpreted and displayed via the native application or web browser 270 of the mobile device 212 or via a web browser (not shown) of the computers 214, 216. It should be understood that it may be desirable for some or all of the data transmitted from the server 202 to the web-enabled device 206-216, or vice versa, to be encrypted and/or otherwise transmitted in a secure manner.

Figure 3:
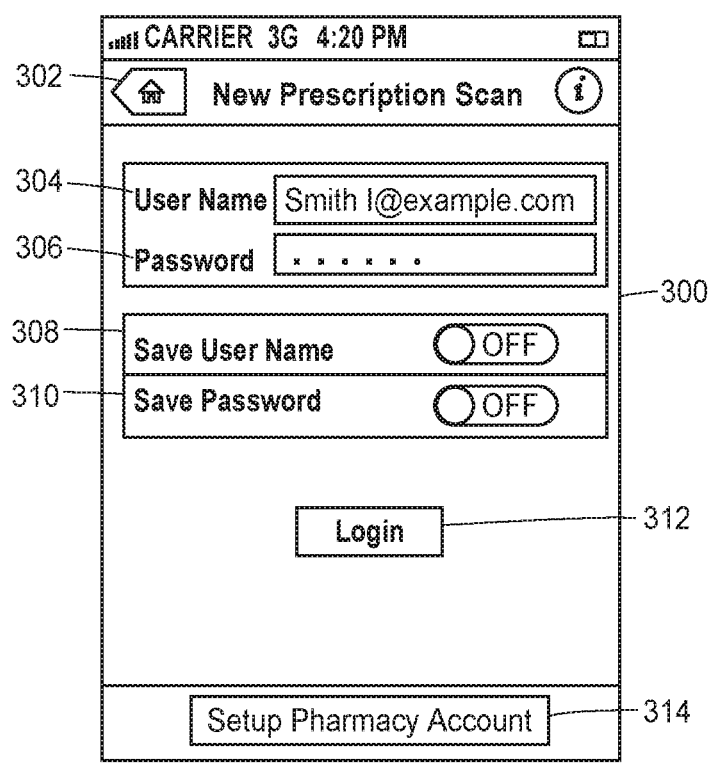
FIG. 3 depicts a login screen of a client application.
Figure 4A:
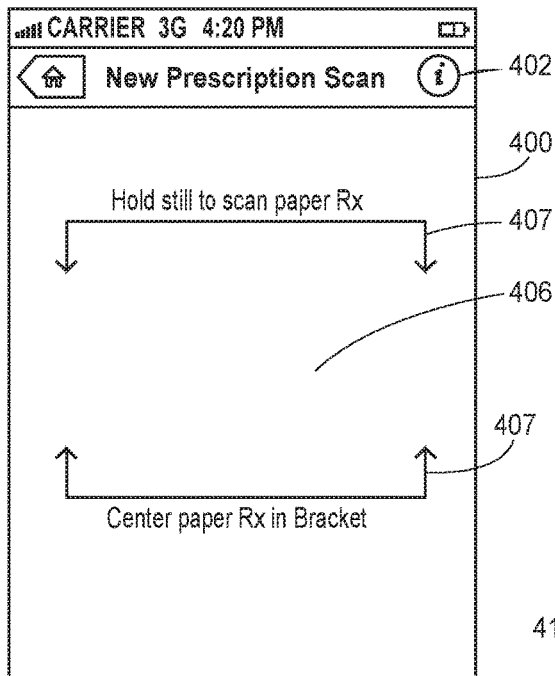
FIG. 4A depicts an image capture screen of a client application in accordance with the presently described embodiments.

In any event, from the home screen 222, the user may select the "New Prescription Scan" link 286 to navigate directly to a login screen 300, as shown in FIG. 3, that may be displayed on the mobile device 212 via the client application 266. When a user launches the "New Prescription Scan" application for the first time, the client application 266 may display a tutorial screen that explains what "New Prescription Scan" is, how "New Prescription Scan" works, and also explains that a user must bring the new paper prescription, handwritten or printed by a healthcare provider, to the pharmacy when picking up the new prescription order. Additionally, this screen may also be displayed when the user selects the information button 402, as depicted in FIG. 4A.

The login screen 300 may include a home button 302 that may cause the client application 266 to return to the home screen 222 of FIG. 2. The login screen 300 also includes an area for logging in to a pharmacy account by entering a username 304 and a password 306. The username and password may be associated with a customer record, such as the customer records stored in the database 146 of FIG. 1A. Alternatively, in some implementations the login screen 300 may not include an area for entering a username 304 and password 306. Instead, the login screen 300 may require the user to enter personal information such as a customer name, a customer birth date and/or a customer address to access a customer record. In other implementations, a user may not be required to login to the system.

The login screen 300 includes an area for saving a username 308 and an area for saving a password 310. The user can select the option to save a username 308 or a password 310 to avoid entering the same username or password the next time the user logs in to the system. Once the user enters a username and password, the user may select a login button 312. After the login button is selected, the server 202 verifies that the username and password corresponds to a customer record from the database 146 of FIG. 1A. If the username and password do not correspond to a customer record, the login screen 300 displays an error message and prompts the user to reenter a username and password. If the user does not have an account, the user may select an option to set up a pharmacy account 314. This option takes the user to a pharmacy registration form application view or web page (not shown) which requires the user to enter personal information as well as insurance information and attempts to match the user to an existing customer record from the database 146. In any event, if there is a successful match or the user has set up a new account, the user is prompted to select a patient for the new prescription order from a stored list of authorized patients in the user's customer record. For example, if the user is a caregiver or a parent of the patient, the user can order the new paper prescription on behalf of the patient by selecting this option. Moreover, the patient may also be the same person as the user. Once a patient is selected, the client application 266 may display an image capture screen 400, such as that depicted in FIG. 4A. Alternatively, the user may be prompted to login to the system after capturing the image using the image capture screen 400.

The image capture screen 400 may include an information button 402 that causes the client application 266 to display instructions associated with the new prescription order system 100, or causes a native application or a web browser of the mobile device to navigate to an application view or a web page containing such instructions. The image capture screen 400 also includes an image capture area 406, which may include an image capture frame indicated by marks 407 on the display. Aligning the new paper prescription within the marks 407 indicated by the image capture frame may cause the application to capture and/or interpret (explained further below) the new paper prescription. Alternatively, a button (not shown), when activated by a user, may cause the image capture device to capture the new paper prescription. In some embodiments, the image capture screen 400 may also capture the front and back of a medical insurance card for a user who does not have insurance information stored in the customer profile or a user with updated insurance information.

Figure 4B:
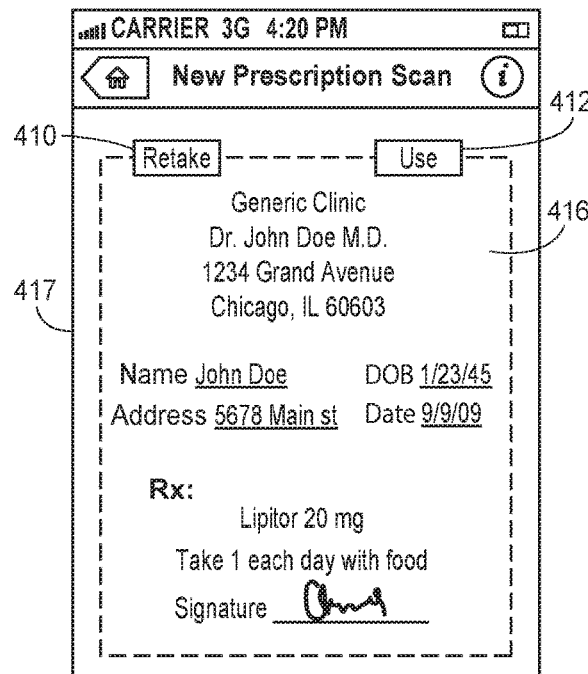
FIG. 4B depicts a screen presenting a captured image to a user in accordance with the presently described embodiments.

After the image is captured, the client application 266 may display a screen 417, as depicted in FIG. 4B. The screen 417 displays the captured image of the new paper prescription 416 to the user and allows for the user to select a "Retake" button 410 or a "Use" button 412. If the user selects the "Retake" button 410, the client application 266 displays the image capture screen 400 of FIG. 4A, prompting the user to capture another image of the new paper prescription. If the user selects the "Use" button 412, the client application 266 transmits the image of the new paper prescription to the server 202.

As used herein, the term "new paper prescription" may be used to refer to any set of handwritten or printed instructions by a prescriber authorizing a patient to be provided a medication or treatment which is not a refill of a previous medication or treatment or the patient does not have any more prescribed refills for the previous medication. Generally, the term "new prescription order" is used to refer to instructions to a pharmacist to fill the new paper prescription at a selected location for picking up the medication corresponding to the new paper prescription and/or a pickup date and time.

Once the new paper prescription image is transmitted, the server 202 determines prescription data from the new paper prescription image. The prescription data generally includes, but is not limited to: a name of the medication; an indication of whether or not a generic may be substituted; a dose (i.e., pills per day) of the medication; a number of days of medication to be dispensed (also referred to herein as a "day supply" or a "prescribed day supply"); a number of refills prescribed; a prescription date; a prescribing physician; a practice name for the prescribing physician; a signature for the prescribing physician; a DEA number for the prescribing physician; a phone number for the prescribing physician; and an address for the prescribing physician. Of course, the prescription data need not include all of the information above. Moreover, the prescription data may include additional information not mentioned above. The server 202 may determine the prescription data from the new paper prescription image through the use of computer vision techniques such as optical character recognition (OCR). For example, OCR may be used to search for prescription data elements such as the prescriber name. In some embodiments, a pharmacist may be required to enter some of the prescription data elements by reading the new paper prescription image.

Figure 4C:
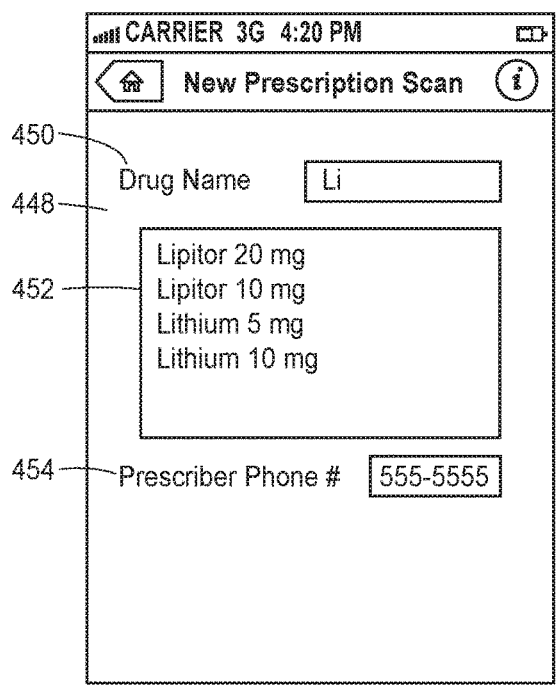
FIG. 4C depicts a medication selection screen of a client application in accordance with the presently described embodiments.
Figure 4D:
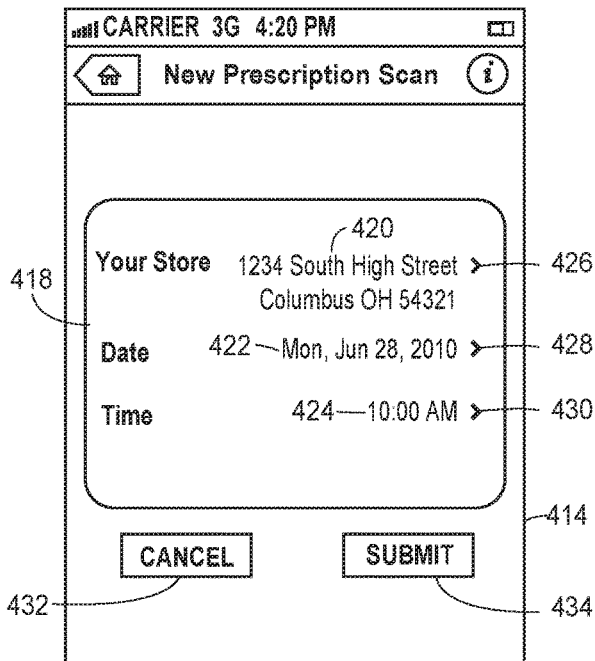
FIG. 4D depicts an order review screen of a client application in accordance with the presently described embodiments.
Figure 4E:
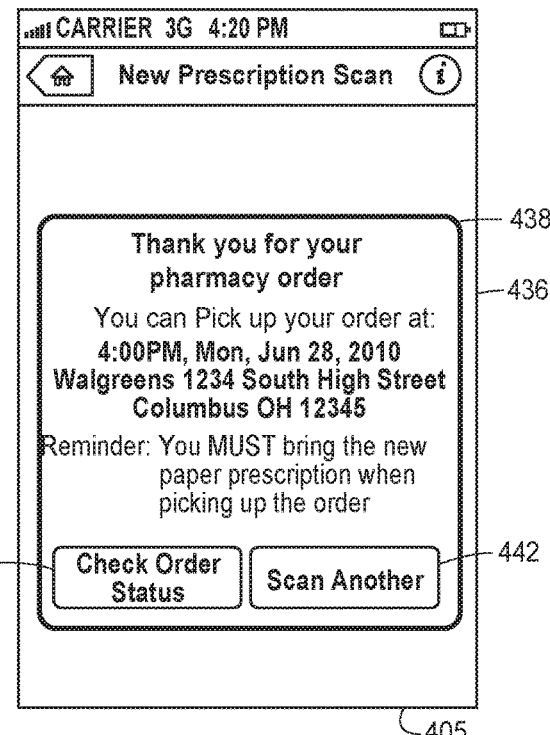
FIG. 4E depicts an order confirmation screen of a client application in accordance with the presently described embodiments.
Figure 4F:
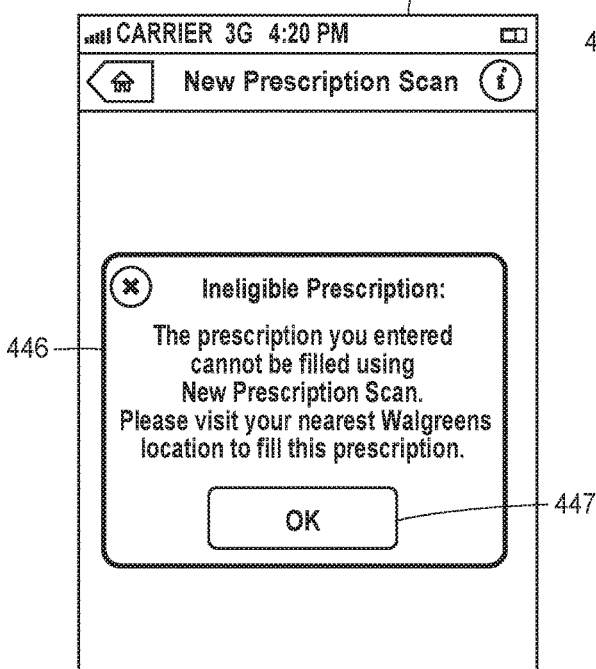
FIG. 4F depicts an error message screen of a client application in accordance with the presently described embodiments.
Figure 4G:
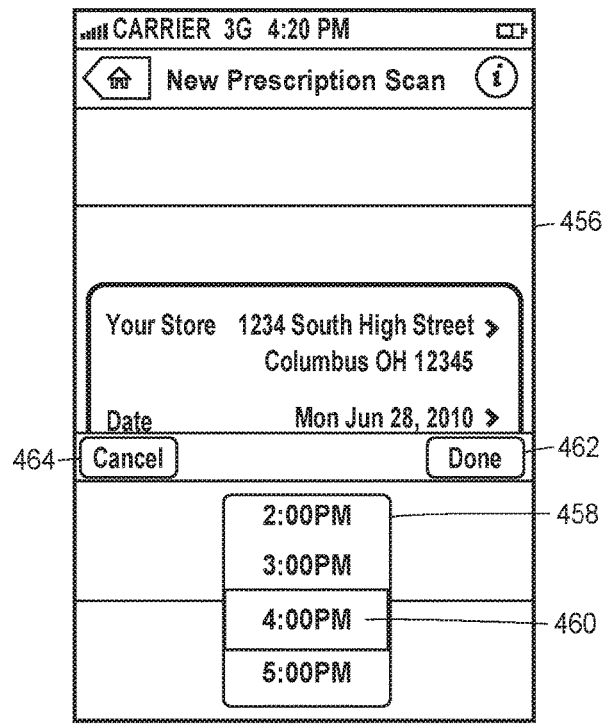
FIG. 4G depicts a pickup time selection screen of a client application in accordance with the presently described embodiments.
Figure 4H:
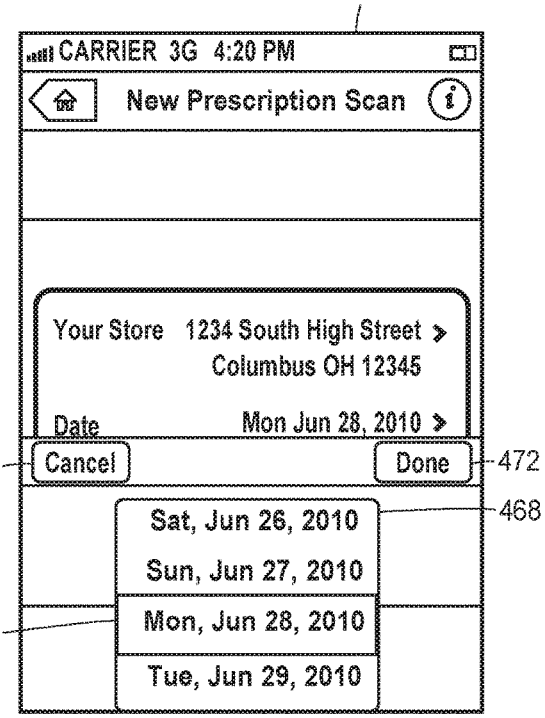
FIG. 4H depicts a pickup date selection screen of a client application in accordance with the presently described embodiments.

In one embodiment, the user selects the name of the medication for the new prescription order. The client application 266 displays a medication selection screen 448, as depicted in FIG. 4C, which includes an area for the user to enter the name of the medication 450. As the user enters the name, a drop-down menu 452 predicts which medication the user may be trying to enter by displaying stored medications from the database 146 starting with the same letters. For example, the user may enter in the letters "Li" causing the drop-down menu to display Lipitor 20 mg, Lipitor 10 mg, Lithium 5 mg, Lithium 10 mg. The user may then select one of the medications from the drop-down menu. If the medication does not appear on the drop-down list or the medication is a controlled substance, the client application 266 may display an error screen 444 as shown in FIG. 4F, which is described in more detail below.

In other embodiments, prescription data may be determined by utilizing a previously stored list of the most frequent prescriptions written or printed by each prescriber. As mentioned above, the database 146 (as shown in FIG. 1A) stores previously written or printed prescriptions which may be used to generate the list of the most frequent prescriptions written or printed by each prescriber. For example, the list may be determined by counting the number of prescriptions having the same medication name, dosage, day supply and number of refills. If, for example, the prescriber writes at least ten such prescriptions within the past year then the prescription is entered into the list of the most frequent prescriptions for the prescriber. However, this is only an example and the list of most frequent prescriptions can be determined in any number of ways. The medication name on the new paper prescription image is then compared to the medication names on the list of most frequent prescriptions for the prescriber. When the medication name on the new paper prescription image matches with a prescription on the list, the server 202 automatically determines the rest of the prescription data for the new paper prescription using prescription data from the matching prescription. For example, if Dr. Smith wrote or printed the new paper prescription and prescribed medicine X, then the dosage, day supply, number of refills etc., for the new paper prescription would be determined based on the dosage, day supply, number of refills etc., for prescribed medicine X which appears on the stored list of most frequent prescriptions for Dr. Smith. Alternatively, prescription data may be determined utilizing a list of most frequent prescriptions when some of the prescription data is missing from the new paper prescription image or the prescription data is unreadable.

Additionally, having transmitted the new paper prescription image to the server 202, the client application 266 receives information back from the server 202 indicating, for example, a default pickup store and a default pickup time and date. The default pickup store may be the store at which previous prescription orders for the user were filled. This information may be displayed by the client application 266 in an order review screen 414, as depicted in FIG. 4D. As FIG. 4D illustrates, the order review screen 414 may display the order information 418. The order information 418 may include the pickup store 420, the pickup date 422, and the pickup time 424. Each of the pickup store 420, the pickup date 422, and the pickup time 424 may have an associated control 426, 428, and 430, respectively, that allows the user to change the corresponding item, as described below. A cancel button 432 may allow the user to cancel the process and return to the home screen, while a submit button 434 allows the user to submit the new prescription order. Additionally, the order review screen 414 may include an option to have the new prescription order delivered in which case the user does not select a default pick up store. If the new prescription is delivered, the user may select an option for same day delivery, express shipping, overnight shipping, etc. In this case, the order review screen 414 may include an option for the user to enter a home address or a shipping address for the new prescription order to be delivered by, for example, a courier service.

In some embodiments, the control 426 that allows the user to change the selected store may activate—or give the user an option to activate—a geolocation device (e.g., a global positioning system (GPS) device) in the web-enabled device 206-216, particularly if the device is a mobile device (e.g., the devices 206-214). The geolocation device may, by itself or cooperating with another application or an online service, provide the client application with an indication of the web-enabled device's current position, which the client application may use to determine the closest store at which the requested prescriptions can be filled.

If the user activates the submit button 434, the web server 202 may submit the new prescription order to the selected pharmacy, to a central database handling prescription processing, to a prescription handling routine, to a prescription processing system, or to any routing or system otherwise appropriately routing the new prescription order. As a result, the client application may display an order confirmation screen 436, such as that depicted in FIG. 4E.

The order confirmation screen 436 may include an order confirmation message 438 including a statement that the user must bring the new paper prescription when picking up the new prescription order. The order confirmation message 438 may also include customer information from the customer record, and the name of the medication. Buttons 440, 442 and 476 may, respectively, allow the user to return to the home screen 222, to scan another new paper prescription or to check the status of the new prescription order. An additional button (not shown) may cause a calendar entry or other reminder to be stored in another application (e.g., a calendar application) on the mobile device. The order confirmation screen 436 may also include an option (not shown) for the user to pay for the new prescription order from the mobile device 212 or a computer. If the user selects this option, the client application 266 may display a prescription payment page (not shown), which may include the option for the user to enter payment information and also may include relevant digital coupons based on the new prescription order. The payment page may also include an option to accept and redeem loyalty rewards program points for placing the new prescription order and can also include an option for the user to sign up for a loyalty rewards program. A loyalty rewards program may be any program offered by a company which provides benefits to customers who frequently make purchases.

If the user selects the check order status button 476, the client application may display an order status page (not shown). The order status page includes a list of order statuses in a linear flow indicating where the order is in the process. For example, the list of order statuses may be: order placed, order received at store, medication in-stock, billing/insurance processed, check for drug interaction, filling prescription and ready for pick-up including the price of the prescription and an indication that the user can pay for the prescription from the mobile device or a computer. Once each of these steps have been completed, the order status page marks the step with, for example, a check mark to indicate to the user that the step has been completed. The order status page may also indicate the amount of time left before the new prescription order is ready.

In addition to the order status page, a user may also receive a series of notifications from the new prescription order system 100 via email, SMS message or any other form of electronic communication. The notifications may be sent to let the user know the new prescription order is ready for pickup. Additionally, the notifications may include a reminder that the user must bring the new paper prescription when picking up the new prescription order.

FIG. 4F depicts an error message 446 that the client application 266 may display on an error screen 444. The error screen 444 may be generated for several reasons. As described in further detail below, if the new prescription order system 100 determines there is a high risk that the new prescription order is fraudulent, the client application 266 may display the error screen 444 to prevent the user from ordering a fraudulent prescription. The error screen 444 may also be generated for other reasons such as the prescription medication is a controlled substance, the prescription data is unreadable because of poor handwriting or a poorly captured image. When a user receives the error message 446, the user may recapture the new paper prescription image and repeat the process of FIGS. 4A-4E or abort the process and call or visit the selected pharmacy. A button 447 allows a user to dismiss the message.

If the user activates the control 424 (FIG. 4D), the client application 266 may display a screen 456 (FIG. 4G) to allow the user to select and/or request a new pickup time. The screen 456 may include a pick up list 458 from which the user may select a time 460 to pick up the new prescription order. Of course, other input means may be used, such as numeric entry fields, radio buttons, etc. When the user has made a selection, the user may activate a button 462 to accept the choice and return to the order review screen 414. Alternatively, the user may activate a cancel button 464 to cancel the request to change the pickup time and return to the order review screen 414.

Similarly, if the user activates the control 422 (FIG. 4D), the client application 266 may display a screen 466 (FIG. 4H) to allow the user to select and/or request a new pickup date. The screen 466 may include a pick up list 468 from which the user may select a date 470 on which to pick up the new prescription order. Of course, other input means may be used, such as numeric entry fields, radio buttons, etc. When the user has made a selection, the user may activate a button 472 to accept the choice and return to the order review screen 414. Alternatively, the user may activate a cancel button 474 to cancel the request to change the pickup time and return to the order review screen 414.

As mentioned above, the new prescription order system 100 also determines whether there is a risk the new prescription order is fraudulent. To determine a risk of fraud, the server 202 determines the locations of: the web-enabled device 206-216 (as shown in FIG. 1B) of the user, the office of the prescriber and the selected pharmacy. These locations can be determined in many ways. For example, the location of the web-enabled device can be determined by reading geolocation information embedded in the captured image of the new paper prescription. Alternatively, if the user gives permission to the new prescription order system 100 to retrieve the user's location, the server 202 may receive location information from the GPS 244 (as shown in FIG. 1D) of the mobile device 212. Moreover, the prescriber's office location may be determined by using the DEA number in the prescription data to retrieve the prescriber's address stored in the database 146 (as shown in FIG. 1A). The prescriber's office location may also be included in the prescription data. Furthermore, the location of the selected pharmacy may be retrieved from the database 146 or the user may enter the location when selecting the pharmacy. However, these are merely examples of how to determine location information. Other methods for determining location information may also be utilized.

Figure 5:
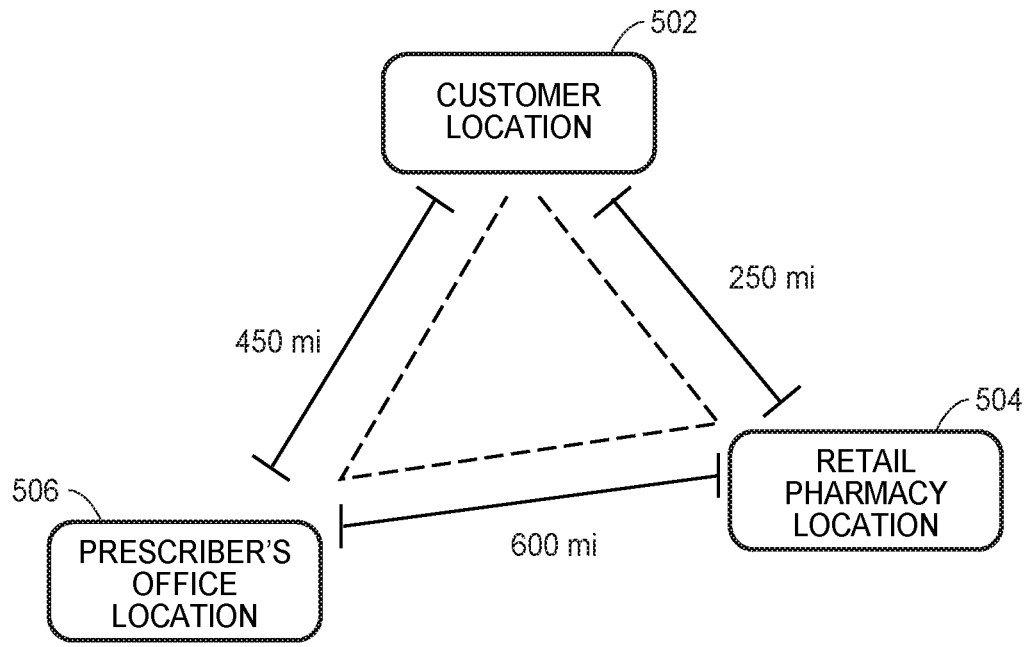
FIG. 5 illustrates a diagram representing the locations of a web-enabled device, a prescriber and a pharmacy.

Once the location information is determined, the new prescription order system 100 calculates the distance between the web-enabled device and the prescriber's office, the prescriber's office and the pharmacy, and/or the web-enabled device and the pharmacy. These distances are illustrated in the diagram of FIG. 5. In the example of FIG. 5, the distance between the customer 502 and the pharmacy 504 is 250 miles. The distance between the pharmacy 504 and the prescriber 506 is 600 miles and the distance between the prescriber 506 and the customer 502 is 450 miles. In one example, the new prescription order system 100 may assign a score representing a risk of fraud based on the average of these distances. In another example, the score may be assigned based on the shortest distance between the three locations. For example, if the customer's location 502 and the prescriber's location 506 are within 2 miles of each other but the customer's location 502 is 500 miles from the pharmacy 504, it is likely that the customer is either out of town or about to be out of town and wants to pick up the new prescription order in a different city from the city in which the customer was prescribed. Unequal weightings may also be applied to each of the determined distances. However, these are merely examples and the risk of fraud score may be assigned in any number of ways. Also, in some implementations only two locations are determined and as a result only one distance is calculated. The one distance is then used to assign the risk of fraud score.

In any event, the risk of fraud score is compared to a predetermined threshold score, i.e., 150. If the risk of fraud score exceeds this threshold, the new prescription order system 100 may transmit an alert to a pharmacist in the selected pharmacy. Also, the new prescription order system 100 may transmit an alert to loss/prevention and compliance officers or may reject the new prescription order. If the new prescription order is rejected the client application 266 may generate the error screen 444 as illustrated in FIG. 4F. The client application 266 may also generate the error screen 444 with the error message 446 telling the user to call or visit the pharmacy when the pharmacist or loss/prevention and compliance officers are alerted. In this manner, the user can discuss with the pharmacist to determine whether the pharmacist believes the new prescription order is fraudulent. Alternatively, the client application 266 may generate a separate message (not shown) on the error screen 444 when an alert is transmitted indicating to the customer that a pharmacist or a loss/prevention and compliance officer must evaluate the new prescription order and will contact the user once it is determined whether the new prescription order is fraudulent.

Figure 6:
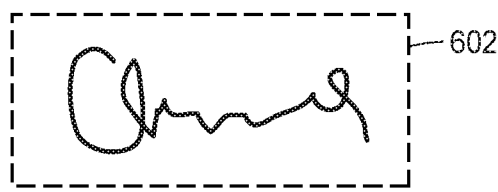
FIG. 6 illustrates an exemplary comparison between a signature on the new prescription order and a prescriber's stored signatures.
Figure 6:
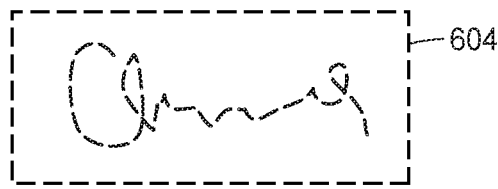

The new prescription order system 100 may also determine a risk of fraud by comparing the prescriber's signature on the new paper prescription to a list of previously stored signatures for the prescriber, as illustrated in FIG. 6. For example, the list of previously stored signatures may be retrieved from the database 146 (as shown in FIG. 1A). The signature on the new paper prescription 602 is then compared with a digital fingerprint 604 derived from each of the signatures on the list of previously stored signatures, using signature recognition techniques. If there is no match between the signature on the new paper prescription 602 and the digital fingerprint 604 or there is no signature on the new paper prescription 602, the client application 266 may generate the error screen 444 as illustrated in FIG. 4F.

In some implementations, instead of rejecting the new prescription order, the new prescription order system 100 may transmit an alert to a pharmacist in the selected pharmacy or an alert to loss/prevention and compliance officer. The client application 266 may also generate the error screen 444 with the error message 446 telling the user to call or visit the pharmacy, when the pharmacist or loss/prevention and compliance officers are alerted. In this manner, the user can discuss with the pharmacist to determine whether the pharmacist believes the new prescription order is fraudulent. Alternatively, the client application 266 may generate a separate message (not shown) on the error screen 444 when an alert is transmitted indicating to the customer that a pharmacist or a loss/prevention and compliance officer must evaluate the new prescription order and will contact the user once it is determined whether the prescription is fraudulent.

In some implementations, the new prescription order system 100 may determine the risk of fraud based on both the distances between the web-enabled device, the prescriber and the pharmacy, and the compared signatures. The new prescription order system 100 may assign a single risk of fraud score and transmit an alert or reject the new prescription order based on this score. In yet another implementation, the new prescription order system 100 may send a single alert based on the risk of fraud score and the compared signatures.

Figure 7:
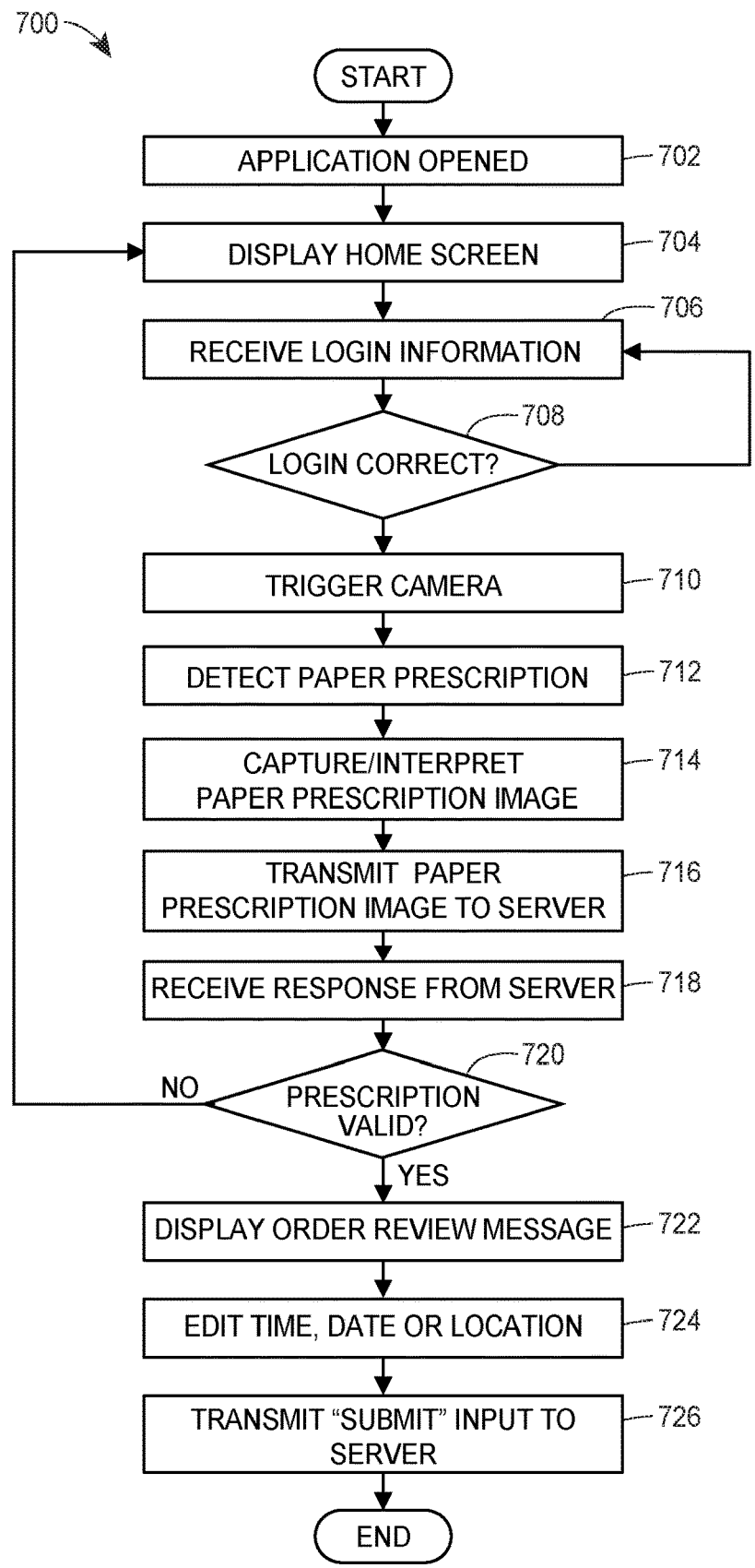
FIG. 7 depicts a flow diagram representing an exemplary client-side method for implementing the new prescription order system in accordance with the presently described embodiments.

FIG. 7 depicts a flow diagram representing an exemplary client-side method 700 for implementing the new prescription order system 100 using a client application 266. The user executes the application (block 702) on the web-enabled device, causing the client application 266 to display a home screen 222 (block 704). From the home screen 222, the user may select to order a new paper prescription using the "New Prescription Scan" link 286. Activation of the new prescription scan service 286 requires the user to enter login information (block 706). The client application 266 then determines if the login information matches with a customer identification in a database (block 708). If a match does not exist, the client application 266 prompts the user to re-enter the login information (block 706). Otherwise, if there is a match the method proceeds to block 710. Alternatively, the client application 266 may capture and/or interpret the new paper prescription before receiving login information. In any event, at block 710, the client application 266 triggers the image capture device. The client application 266 may automatically detect the new paper prescription (block 712) when the new paper prescription is within the view of the image capture device. The client application 266 thereafter captures and/or interprets the new paper prescription (block 714) and transmits the image of the new paper prescription to the server 202 (block 716). The server 202 may interpret the new paper prescription image into prescription data and send a response to the client application 266 (block 718). If the response indicates that the new prescription order is invalid, either because there is a high risk that the new prescription order is fraudulent, there is an error in the prescription data or the prescription medication is a controlled substance, the client application 266 may display an error (block 720) and return to the home screen (block 704). If the new prescription order is valid, the client application may display an order review message (block 722), such as the order review screen 414 depicted in FIG. 4D. The user may edit the time and/or date at which the new prescription order will be ready to be picked up, and/or may edit the location at which the new prescription order will be filled (block 724). Once the user has done so, or if the user does not do so, the client application 266 transmits a "submit" input to the server (block 726).

Figure 8:
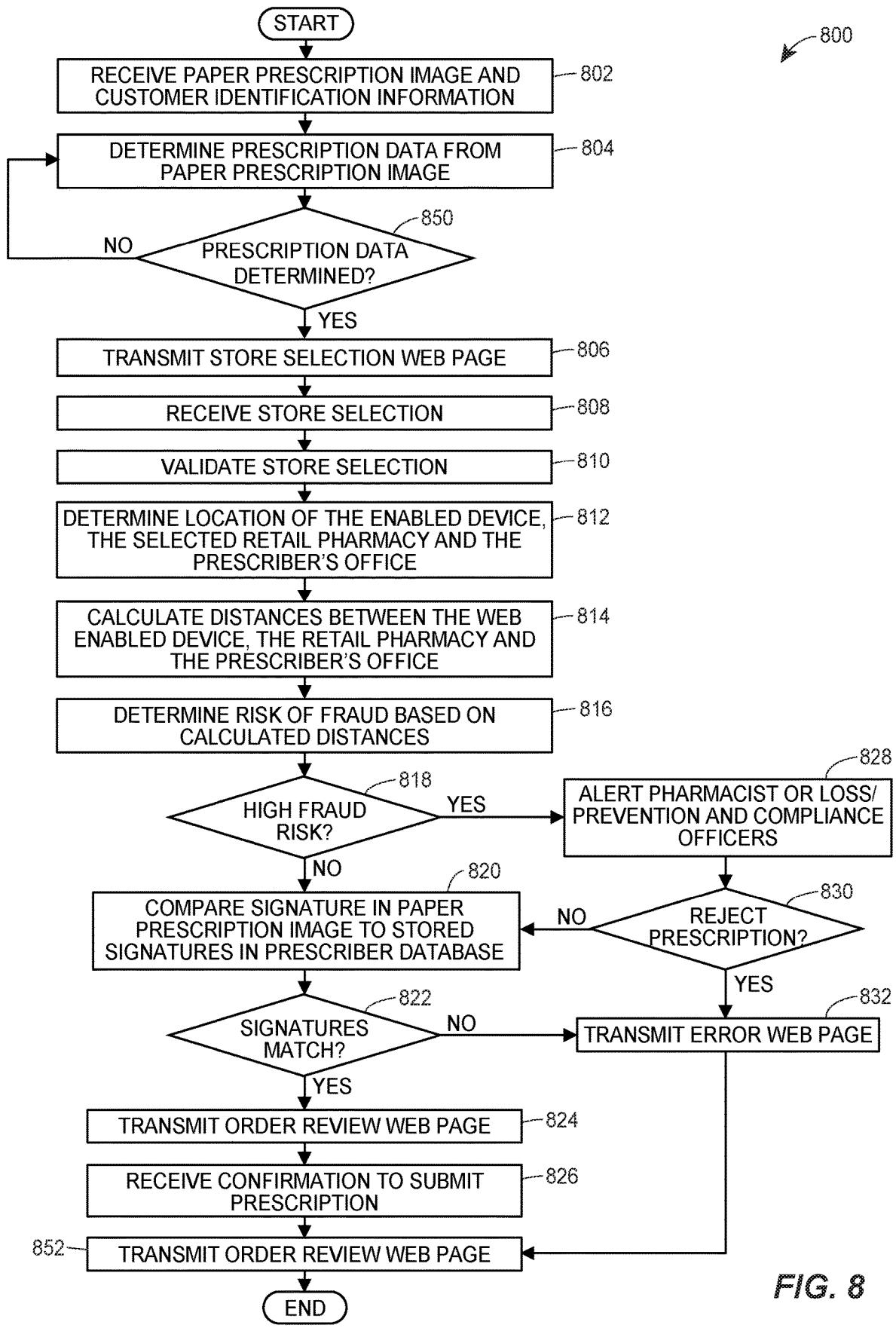
FIG. 8 depicts a flow diagram representing an exemplary server-side method for implementing the new prescription order system in accordance with the presently described embodiments.

FIG. 8 depicts a flow diagram representing an exemplary server-side method 800 for implementing the new prescription order system 100 using a client application 266. The server 202 receives a new paper prescription image along with customer identification information corresponding to the user's login information (block 802). From the new paper prescription image, the server 202 determines prescription data (block 804). If all of the prescription data to fill the new prescription order has not been determined the server repeats block 804 or generates an error message such as the error screen 444 depicted in FIG. 4F and either ends the process or requires a pharmacist to determine the remaining prescription data. If all of the prescription data to fill the new prescription order has been determined, the server 202 transmits a store selection web page or application view (block 806) allowing the user to a select a pharmacy for picking up the new prescription order or having the new prescription order delivered. As a result, the server 202 receives the user's pharmacy selection (block 808) and validates the selected pharmacy (block 810) to make sure the pharmacy carries the prescription medication or a generic substitute if allowed, and that the pharmacy is still at the selected location. Once the pharmacy is validated, the server 202 determines the location of the web-enabled device, the selected pharmacy and the office of the prescriber who wrote or printed the new paper prescription (block 812). The locations are then utilized to calculate the distances between the three locations (block 814). Based on the calculated distances, the server 202 determines a risk that the new prescription order is fraudulent (block 816). If the risk of fraud is high, the server 202 alerts a pharmacist in the selected pharmacy or loss/prevention and compliance officer (block 828). The server 202 then determines whether to reject the new prescription order (block 830), based on the pharmacist, the loss compliance officer or the risk of fraud alone. If the new prescription order is rejected, the server transmits an error message (block 832), such as the error screen 444 depicted in FIG. 4F and ends the process. Otherwise, if the new prescription order is not rejected, the server 202 compares the prescriber's signature on the new paper prescription to previously stored signatures for the prescriber in a database 146 (block 820). If the signature on the new prescription does not match with one of the previously stored signatures, the server 202 transmits an error message (block 832), such as the error screen 444 depicted in FIG. 4F and ends the process. Otherwise, if there is a match the server may transmit an order review web page or application view (block 824), such as the order review screen 414 depicted in FIG. 4D. The server 202 then receives confirmation to submit the new prescription order to a pharmacist (block 826) and transmits an order confirmation web page or application view (block 852), such as the order confirmation screen 436 depicted in FIG. 4E.

Figure 9:
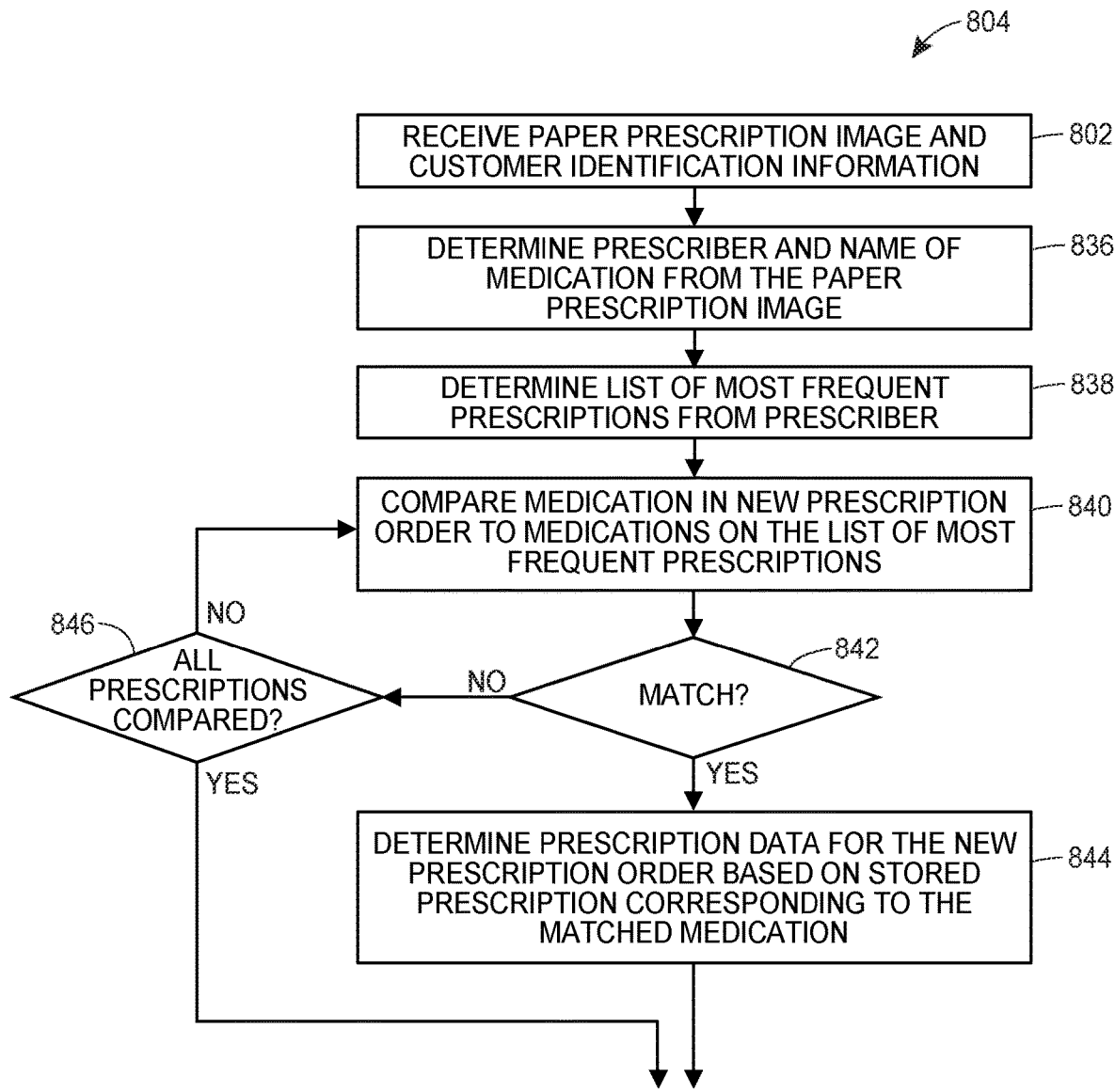
FIG. 9 depicts a flow diagram representing a portion of the server-side method depicted in FIG. 8.

FIG. 9 depicts a flow diagram representing an exemplary method corresponding to the blocks 802-804 of FIG. 8. As described above, the server 202 receives a new paper prescription image along with customer identification information corresponding to the user's login information (block 802). From the new paper prescription image, the server 202 determines the prescriber who wrote or printed the new paper prescription and the name of the prescribed medication (block 836). The server 202 then determines a list of most frequent prescriptions by the prescriber who wrote or printed the new paper prescription (block 838), by looking up the prescriber's previous prescriptions in the database 146 (as shown in FIG. 1A). Using this list, the server 202 compares the prescribed medication from the new paper prescription to each of the medications on the list of most frequent prescriptions for the prescriber (block 840). If there is no match, the server 202 determines whether all of the prescriptions have been compared (block 846). If all of the prescriptions have been compared, the server 202 concludes the medication on the new paper prescription is not amongst the prescriber's most frequent prescriptions and continues on to block 850 of FIG. 8. On the other hand, if there are more prescriptions on the most frequent list that have not been compared, the server continues to compare the medication on the new paper prescription to medications on the list (block 840). If the server 202 does detect a match, then the prescription data for the new paper prescription is automatically determined based on the prescription data for the stored prescription corresponding to the matched medication on the list of most frequent prescriptions (block 844) and the process continues to block 850 of FIG. 8.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A method of detecting fraud when filling a new prescription order for one or more prescription medications, the method executed by one or more computer processors programmed to perform the method, the method comprising:
    storing, for each of a plurality of prescribers, one or more signatures associated with a prescriber;
    receiving, at the one or more processors, from a web-enabled device of a customer, over a network, an image of a new paper prescription for the customer;
    determining, by the one or more processors, a pharmacy at which to fill a new prescription order corresponding to the new paper prescription;
    determining, by the one or more processors, prescription data based on the image of the new paper prescription, wherein the prescription data includes an identification of a prescriber who wrote or printed the new paper prescription;
    comparing, by the one or more processors, a signature in the image of the new paper prescription to the one or more stored signatures associated with the prescriber;
    determining, by the one or more processors, a first risk of prescription fraud based on the compared signatures;
    determining, by the one or more processors, a location of the web-enabled device, a location of the pharmacy, and a location of the prescriber;
    determining, by the one or more processors, a second risk of prescription fraud by assigning weights to a plurality of distances between the location of the web-enabled device, the location of the pharmacy, and the location of the prescriber and combining the plurality of distances and the assigned weights to generate a score indicative of the second risk of prescription fraud;
    combining, by the one or more processors, the first and seconds risks of prescription fraud to generate an overall risk of prescription fraud;
    when the overall risk of prescription fraud does not exceed a threshold amount of risk, transmitting, from the one or more processors and via the network, information to be displayed in an order review page on the web-enabled device; and
    receiving, at the one or more processors, from the web-enabled device and via the network, a confirmation to submit the new prescription order.

2. The method of claim 1, wherein the image of the new paper prescription is captured via an image capture screen, and wherein the confirmation to submit the new prescription order is received via an order review screen.

3. The method of claim 1, wherein determining a pharmacy at which to fill the new prescription order comprises retrieving from a database, for each customer identifier, a record storing a default pharmacy.

4. The method of claim 1, wherein determining a pharmacy at which to fill the new prescription order comprises:
    receiving geolocation information generated by a geolocation device;
    determining one or more pharmacies within a predetermined distance from a location indicated by the geolocation information; and
    receiving a selection by the customer of one of the one or more pharmacies.

5. The method of claim 1, wherein prescription data includes at least one of a practice name, a prescriber name, a prescriber signature, a prescriber phone number, a prescriber address, a DEA number, a dosage, a day supply, a number of refills prescribed, or a prescription date.

6. The method of claim 1, wherein when the score indicative of the second risk of prescription fraud exceeds a predetermined number:
transmitting, from the one or more processors and via the network, at least one of an alert to a pharmacist in the pharmacy, an alert to a loss/prevention and compliance officer, or a rejection of the new prescription order.

7. The method of claim 1, wherein transmitting information to be displayed in an order review page comprises transmitting data corresponding to the pharmacy, a default pickup time and a default pickup date.

8. The method of claim 1, further comprising:
electronically transmitting, from the one or more processors and via the network, the new prescription order to the selected pharmacy; and
electronically notifying, by the one or more processors and via the network, the customer that the new prescription order is ready to be picked up.

9. The method of claim 1, further comprising:
storing, for each of a plurality of prescribers, one or more prescriptions written or printed by a prescriber, wherein each prescription is for one or more prescription medications; and
determining, by the one or more processors, for the prescriber who wrote or printed the new paper prescription, a list of one or more prescriptions which the prescriber prescribes most frequently.

10. The method of claim 9, further comprising:
determining, by the one or more processors, whether a prescription medication in the new paper prescription is the same as one of the one or more prescription medications in the list; and
when the prescription medication in the new paper prescription is the same as one of the one or more prescription medications in the list:
determining, by the one or more processors, prescription data based on a stored prescription for the one of the one or more prescription medications in the list.

11. A system for detecting fraud when filling a new prescription order for one or more prescription medications, the system comprising:
a communication network; and
one or more server computers communicatively coupled to the communication network, at least one of the server computers configured to:
store for each of a plurality of prescribers, one or more signatures associated with a prescriber;
receive from a web-enabled device communicatively coupled to the communication network, an image of a new paper prescription for a customer;
determine a pharmacy at which to fill a new prescription order corresponding to the new paper prescription;
determine prescription data based on the image of the new paper prescription, wherein the prescription data includes an identification of a prescriber who wrote or printed the new paper prescription;
compare a signature in the image of the new paper prescription to the one or more stored signatures associated with the prescriber;
determine a first risk of prescription fraud based on the compared signatures;
determine a location of the web-enabled device, a location of the pharmacy, and a location of the prescriber;
determine a second risk of prescription fraud by assigning weights to a plurality of distances between the location of the web-enabled device, the location of the pharmacy, and the location of the prescriber and combining the plurality of distances and the assigned weights to generate a score indicative of the second risk of prescription fraud;
combine the first and seconds risks of prescription fraud to generate an overall risk of fraud;
when the overall risk of prescription fraud does not exceed a threshold amount of risk, transmit to the web-enabled device from the server computer, via the network, information to be displayed in an order review page on the web-enabled device; and
receive from the web-enabled device, via the network, a confirmation to submit the new prescription order.

12. The system of claim 11, wherein the image of the new paper prescription is captured via an image capture screen, and wherein the confirmation to submit the new prescription order is received via an order review screen.

13. The system of claim 11, wherein to determine a pharmacy at which to fill the new prescription order, the server computer is configured to retrieve from a database, for each customer identifier, a record storing a default pharmacy.

14. The system of claim 11, wherein to determine a pharmacy at which to fill the new prescription order, the server computer is configured to:
receive from the web-enabled device, via the network, geolocation information generated by a geolocation device;
determine one or more pharmacies within a predetermined distance from a location indicated by the geolocation information; and
receive from the web-enabled device, via the network, a selection by the customer of one of the one or more pharmacies.

15. The system of claim 11, wherein prescription data includes at least one of a practice name, a prescriber name, a prescriber signature, a prescriber phone number, a prescriber address, a DEA number, a dosage, a day supply, a number of refills prescribed, or a prescription date.

16. The system of claim 11, wherein when the score indicative of the second risk of prescription fraud exceeds a predetermined number, the server computer is configured to:
transmit via the network, at least one of an alert to a pharmacist in the pharmacy, an alert to a loss/prevention and compliance officer, or a rejection of the new prescription order.

17. The system of claim 11, wherein to transmit information to be displayed in an order review page, the server computer is configured to transmit data corresponding to the pharmacy, a default pickup time and a default pickup date.

18. The system of claim 11, wherein the server computer is further configured to:
electronically transmit, to the web-enabled device from the server computer, via the network, the new prescription order to the selected pharmacy; and
electronically notify, the customer from the server computer, via the network, that the new prescription order is ready to be picked up.

19. The system of claim 11, wherein the server computer is further configured to:
store for each of a plurality of prescribers, one or more prescriptions written or printed by a prescriber, wherein each prescription is for one or more prescription medications; and determine for the prescriber who wrote or printed the new paper prescription, a list of one or more prescriptions which the prescriber prescribes most frequently.

20. The system of claim 19, wherein the server computer is further configured to:
  determine whether a prescription medication in the new paper prescription is the same as one of the one or more prescription medications in the list; and
  when the prescription medication in the new paper prescription is the same as one of the one or more prescription medications in the list:
    determine prescription data based on a stored prescription for the one of the one or more prescription medications in the list.

\* \* \* \* \*